(12) United States Patent
Yoo et al.

(10) Patent No.: US 9,901,525 B2
(45) Date of Patent: Feb. 27, 2018

(54) **EXTERNAL USE SKIN COMPOSITION, CONTAINING *LENTINULA EDODES*-DERIVED ERGOSTEROL**

(71) Applicant: Amorepacific Corporation, Seoul (KR)

(72) Inventors: Sejin Yoo, Yongin-si (KR); Nokhyun Park, Yongin-si (KR); Seokyun Baek, Yongin-si (KR); Songseok Shin, Yongin-si (KR); Jonhwan Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 14/900,277

(22) PCT Filed: Jun. 24, 2014

(86) PCT No.: PCT/KR2014/005594
§ 371 (c)(1),
(2) Date: Dec. 21, 2015

(87) PCT Pub. No.: WO2014/208990
PCT Pub. Date: Dec. 31, 2014

(65) Prior Publication Data
US 2016/0151268 A1    Jun. 2, 2016

(30) Foreign Application Priority Data

Jun. 24, 2013 (KR) .................. 10-2013-0072047
Jun. 24, 2013 (KR) .................. 10-2013-0072052

(51) Int. Cl.
  *A61K 8/63* (2006.01)
  *A61Q 19/02* (2006.01)
  *A61K 31/58* (2006.01)

(52) U.S. Cl.
  CPC ............ *A61K 8/63* (2013.01); *A61K 31/58* (2013.01); *A61Q 19/02* (2013.01)

(58) Field of Classification Search
  CPC .......... A61K 8/63; A61K 8/975; A61K 31/58; A61Q 19/02

USPC ................................................ 424/62
See application file for complete search history.

(56) References Cited

U.S. PATENT DOCUMENTS 5,552,147 A  *  9/1996  Znaiden ............... A61K 8/365
                                                    424/401
2005/0191385 A1   9/2005  Amato

FOREIGN PATENT DOCUMENTS

| KR | 10-2005-0080111 A | 8/2005 |
| KR | 10-2006-0020199 A | 3/2006 |
| KR | 10-2010-0083203 A | 7/2010 |
| KR | 10-2010-0097857 A | 9/2010 |
| KR | 20130029294 A1 * | 3/2013 |

OTHER PUBLICATIONS

Liu, Li et al; Title: Scabronine M, a novel inhibitor of NGF-induced neurite outgrowth from PC12 cells from the fungus Sarcodon scabrosus, published online Feb. 20, 2012.*
Yaoita et al, title: Sterol constituents from seven mushrooms; Chemical and Pharmaceutical Bulletin, vol. 47, No. 6, p. 847-851, published 1999*
Unknown author, title: ppm—parts per million. Downloaded from http://www.rapidtables.com/math/number/PPM.htm on Jan. 10, 2017.*
Rathee, Sushila et al., "Mushrooms as therapeutic agents", Revista Brasileira de Farmacognosia Brazilian Journal of Pharmacognosy, Oct. 21, 2011, pp. 459-474, vol. 22, No. 2.
International Searching Authority, International Search Report of PCT/KR2014/005594 dated Oct. 27, 2014.

* cited by examiner

*Primary Examiner* — Yanzhi Zhang
(74) *Attorney, Agent, or Firm* — Sughrue Mion, PLLC

(57) ABSTRACT

The present invention relates to a skin external composition, containing a *Lentinula edodes*-derived material, and more specifically, to an external use skin preparation composition containing an ergosterol-based compound obtained by being isolated from a *Lentinula edodes* extract and purified, thereby showing remarkable whitening effects.

3 Claims, 4 Drawing Sheets

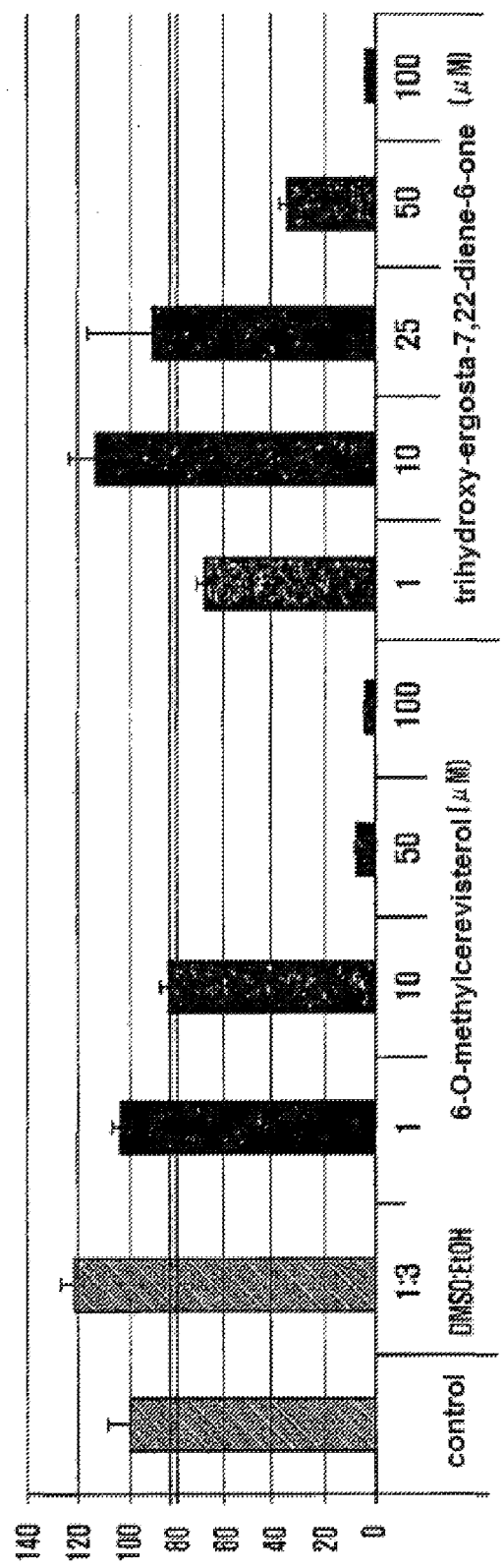
[FIG. 1]

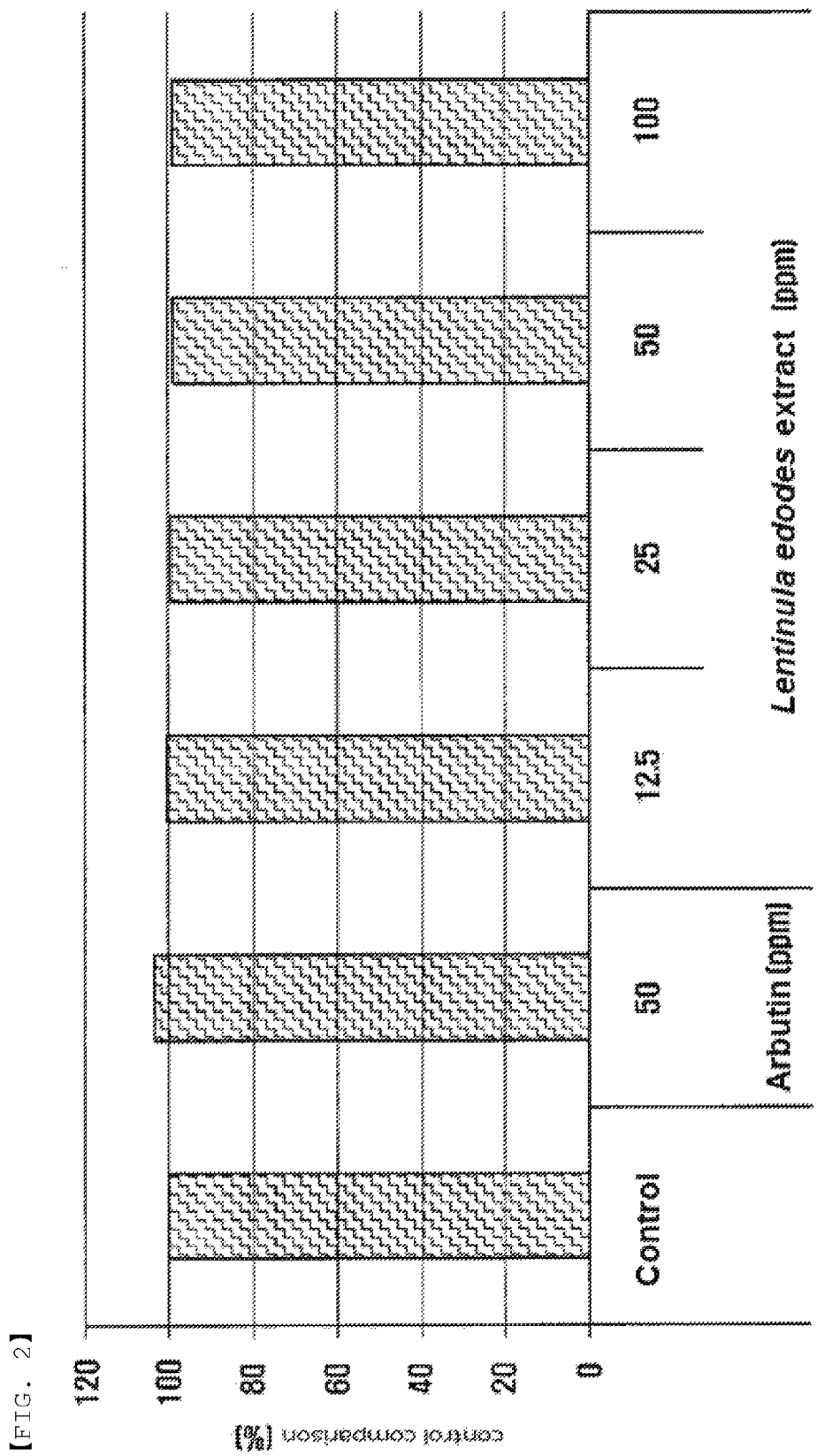
[FIG. 2]

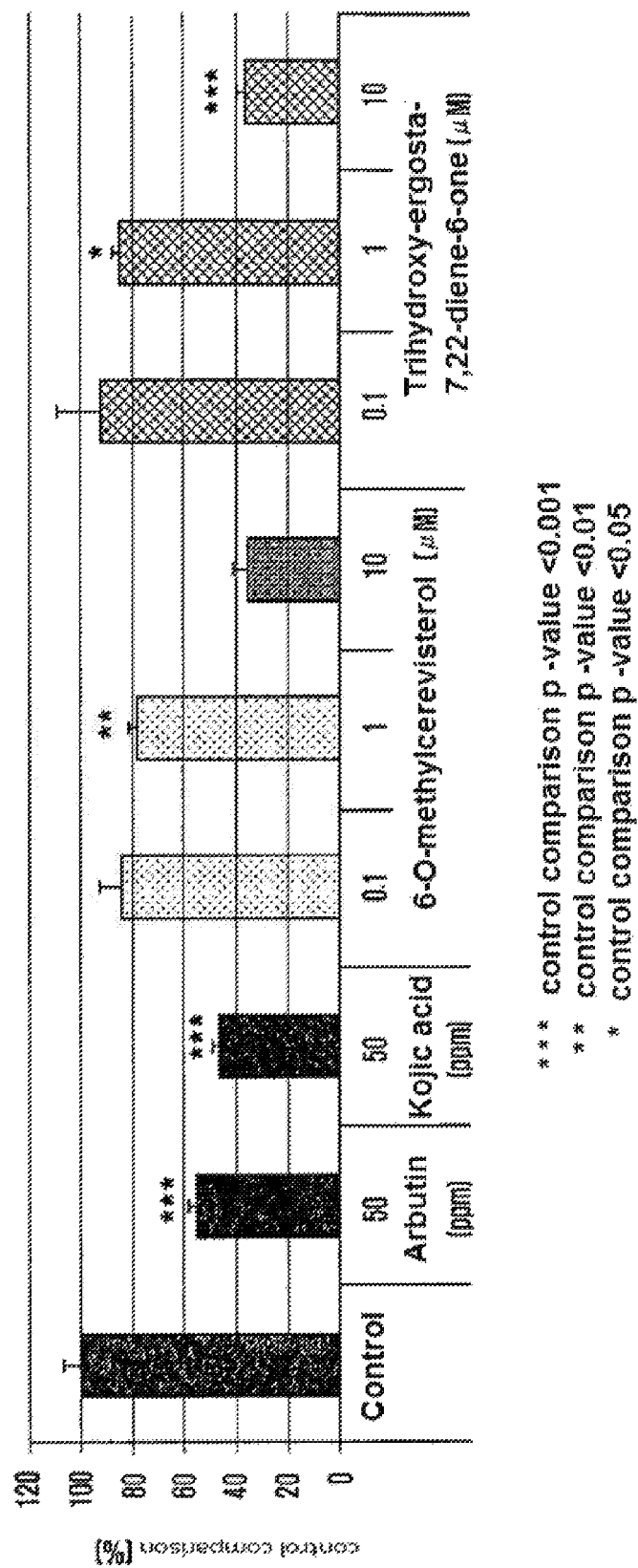
[FIG. 3]

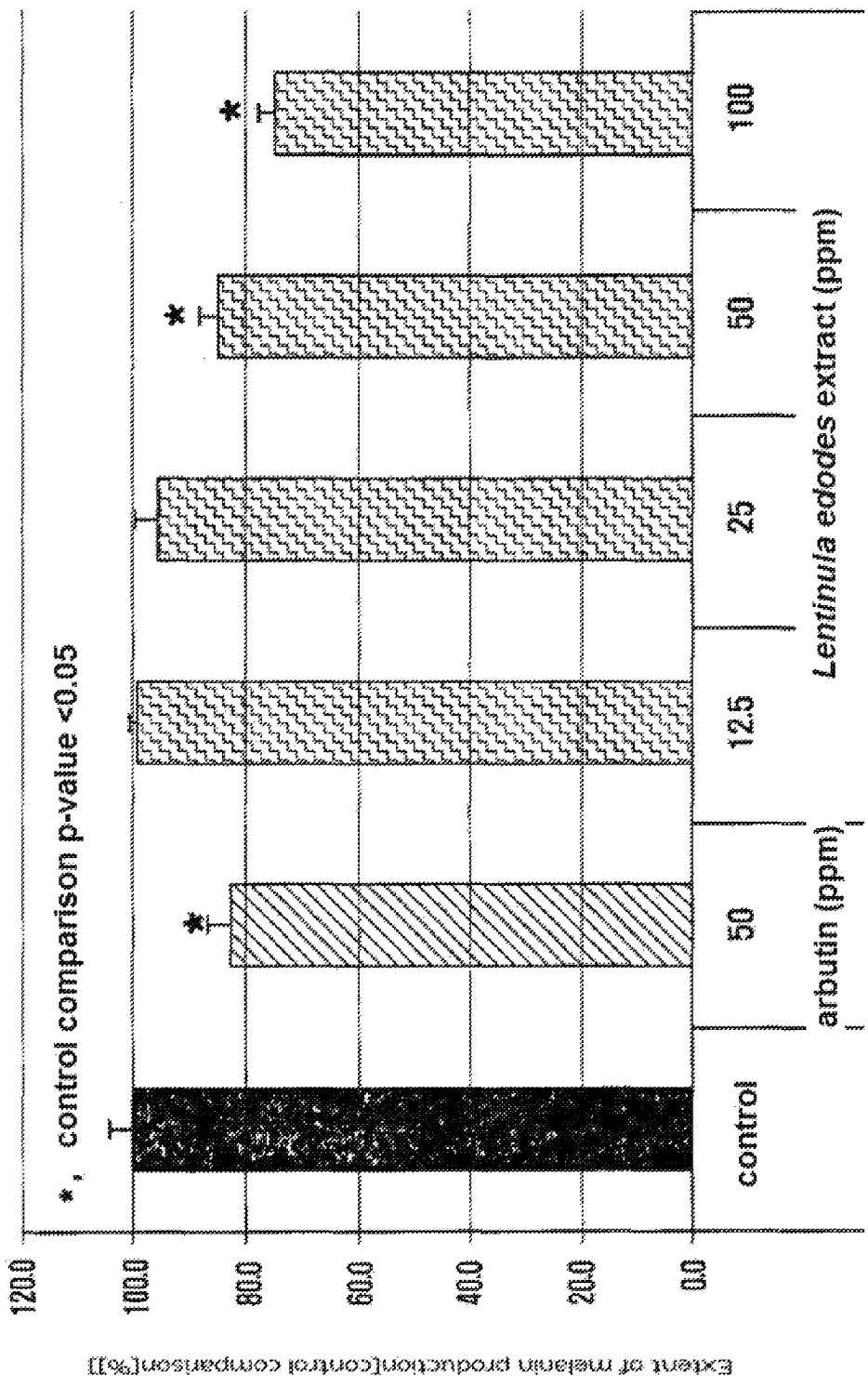
[FIG. 4]

EXTERNAL USE SKIN COMPOSITION, CONTAINING *LENTINULA EDODES*-DERIVED ERGOSTEROL

CROSS REFERENCE TO RELATED APPLICATIONS

This application is a National Stage of International Application No. PCT/KR2014/005594 filed Jun. 24, 2014, claiming priority based on Korean Patent Application Nos. 10-2013-0072047 filed Jun. 24, 2013 and 10-2013-0072052 filed Jun. 24, 2013, the contents of all of which are incorporated herein by reference in their entirety.

TECHNICAL FIELD

The present invention relates to an skin external composition, containing a *Lentinula edodes*-derived material, and more specifically, to an external use skin preparation composition containing an ergosterol-based compound obtained by being isolated from a *Lentinula edodes* extract and purified, thereby showing remarkable whitening effects.

BACKGROUND ART

A skin color of a human is decided by many factors such as an activity of melanocyte which makes a melanin pigment, a distribution of the blood vessels, dermal thickness, and whether the pigment such as carotinoid, bilirubin and the like is contained or not in and out of the human body. In particular, a black pigment such as a melanin which is generated by an action of various enzymes such as tyrosinase, and the like in a melanocyte is the most important factor. A genetic factor, physiological factor related to a hormone excretion, stress, etc. and an environmental factor such as ultraviolet irradiation, and the like are effect to the formation of pigment. Melanin is present in the skin and plays an important role in protecting the body from the ultraviolet radiation and the like, but is known to faciliate the pigment deposition and the skin aging and to play an important role in causing a skin cancer if it is overproduced. In order to treat or reduce the excessive melanin pigment deposition, ascorbic acid, kojic acid, arbutin, hydroquinone, glutathione or their derivatives, and materials having tyrosinase an inhibitory activity have been already combined and used in cosmetics or medicine, but their uses have been limited due to an insufficient whitening effect, safety problem for the skin, safety problem in the formulation when they are combined in cosmetic ingredients, and the like.

DISCLOSURE

Technical Problem

Therefore, inventors of the present invention tried to find ingredients exhibiting the whitening effect in natural substances, and found that 3β, 5α-dihydroxy-6β-methoxy-(22E, 24R)-ergosta-7,22-diene (generally, it has been known as 6-O-methylceresterol) and 3β, 5α, 9α-trihydroxy-(22E, 24R)-ergosta-7,22-diene-6-one which are ergosterol-based compounds extracted from *Lentinula edodes* can provide remarkable whitening effects, and then completed the present invention.

Accordingly, the object of the present invention is to provide a skin external composition containing *Lentinula edodes*-derived materials, thereby showing remarkable skin whitening effects.

Technical Solution

To accomplish the above-mentioned object, the present invention provides a skin external composition for whitening, containing at least of one selected from 3β, 5α-dihydroxy-6β-methoxy-(22E, 24R)-ergosta-7,22-diene and 3β, 5α, 9α-trihydroxy-(22E, 24R)-ergosta-7,22-diene-6-one as an effective ingredient.

Advantageous Effects

The composition according to the present invention can provide whitening effects which are safe and remarkable to the skin by using 3β, 5α-dihydroxy-6β-methoxy-(22E, 24R)-ergosta-7,22-diene or 3β, 5α, 9α-trihydroxy-(22E, 24R)-ergosta-7,22-diene-6-one as an effective ingredient.

DESCRIPTION OF DRAWINGS

FIG. 1 shows the toxicity of 3β, 5α-dihydroxy-6β-methoxy-(22E, 24R)-ergosta-7,22-diene (designated as 6-O-methylcerevisterol) or 3β, 5α, 9α-trihydroxy-(22E, 24R)-ergosta-7,22-diene-6-one (designated as trihydroxy-ergosta-7,22-diene-6-one) to cells which is expressed as the survival rate of cells, measured by MTT analysis.

FIG. 2 shows the toxicity of 70% ethanol extracts of *Lentinula edodes* and arbutin to cells which is expressed as the survival rate of cells, measured by MTT analysis.

FIGS. 3 and 4 show the impact of 3β,5α-dihydroxy-6β-methoxy-(22E, 24R)-ergosta-7,22-diene (designated as 6-O-methylcerevisterol) and 3β,5α,9α-trihydroxy-(22E, 24R)-ergosta-7,22-diene-6-one (designated as trihydroxy-ergosta-7,22-diene-6-one), arbutin, kojic acid and 70% ethanol extract of *Lentinula edodes* on inhibiting melanin production.

BEST MODE FOR INVENTION

The skin external composition of the present invention contains ergosterol-based compound as an effective ingredient, and especially contains ergosterol-based compound extracted from *Lentinula edodes* as the effective ingredient. Specifically, ergosterol-based compound used in the composition of the present invention is 3β, 5α-dihydroxy-6β-methoxy-(22E, 24R)-ergosta-7,22-diene (it is generally known as 6-O-methylcerevisterol) represented by the Chemical Formula 1:

[Chemical Formula 1]

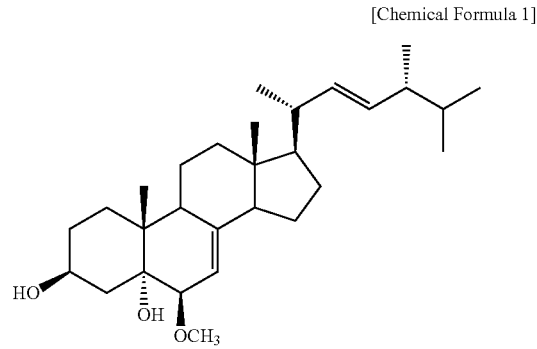 [SMILES: CO[C@@H]1C=C2C3CC[C@H]([C@H](C)/C=C/[C@H](C)C(C)C)[C@@]3(C)CCC2[C@@]2(C)CC[C@H](O)C[C@]12O]

or 3β, 5α, 9α-trihydroxy-(22E, 24R)-ergosta-7,22-diene-6-one represented by the Chemical Formula 2

[Chemical Formula 2]

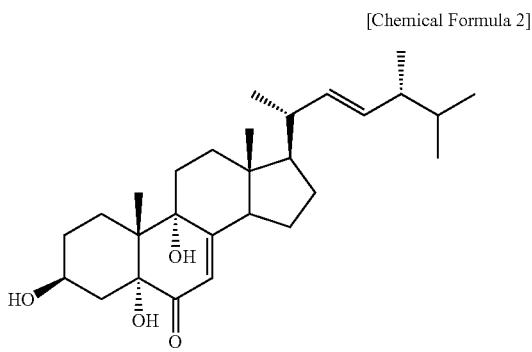

or their mixtures.

*Lentinula edodes* (Nomenclature: *Lentinula edodes* (Berk.) Sing.) belongs to *Lentinula* genus of Tricholomataceae family, and is the mushroom which grows as the most whitest one among shiitakes, and has been known as having an effectiveness regarding an action promoting a blood circulation, anti-cancer effect, anti-oxidation effect, prevention of anemia, cholesterol, hypertension and osteoporosis, and the like.

*Lentinula edodes* contains lots of vitamins, especially a precursor of vitamin D, ergosterol as ingredients, and also contains a considerable amount of vitamins B1 and B2. Taste component is Guanylic acid, an aroma component is a compound having sulfur, lethionin, and in addition to that, glyholin, coriolin, illudin, eritadenine, β-Glucan, and the like are contained.

3β, 5α-Dihydroxy-6β-methoxy-(22E, 24M-ergosta-7,22-diene or 3β, 5α, 9α-trihydroxy-(22E, 24R)-ergosta-7,22-diene-6-one as used in the present invention can be obtained by being isolated from *Lentinula edodes* and purified, and briefly, the extract is obtained from *Lentinula edodes* by using 70% ethanol, dried and pulverized, and then the obtained extracts are distributed and extracted by using ethyl acetate to isolate a single component.

The effective ingredients as mentioned above are contained in an amount of 10 ppm~50,000 ppm to the total of weight of the composition in the composition of the present invention. If the content is less than 10 ppm, the whitening effect is not exhibited, and if the content is greater than 50,000 ppm, the skin stimulation is occurred.

In addition, the composition of the present invention can contain the known material exhibiting the whitening effect. Specifically, it can further contain at least one selected from the group consisting of ascorbyl glucoside, licorice extract, arbutin, ascorbic acid, kojic acid, niacin amide, oleanolic acid, etc., and they are contained in an amount of 0.01-5.0 weight percent (wt %) to the total of weight of the composition. It is because of that if they are contained in an amount of less than 0.01 wt %, since they are absorbed into the skin, they can not exhibit their efficiency, and if they are contained in an amount of greater than 5.0 wt %, since they exhibit toxicity to the skin or stickiness of the skin is greatly increased, it is difficult to exhibit a value as an external use skin preparation.

The composition of the present invention exhibits Detox efficiency by purifying contaminants on the skin and by making the skin clear, and can realize the whitening effect by brightly improving a dull skin.

The composition according to the present invention can be formulated by containing the cosmetologically or dermatologically acceptable medium or base. It can be provided as all of the formulation suitable for a topical application, for example, as a form of emulsion, suspension, microemulsion, microcapsule, microgranule or ionic form (liposome) and vesicle dispersion of non-ionic form, or as a form of cream, skin, lotion, powder, ointment, spray or conceal stick. In addition, it can be used as the form of foam or the form of aerosol composition which further contains the compressed propellant. The composition can be prepared by the ordinary skill in the art.

In addition, the composition according to the present invention can contain adjuvants which are commonly used in cosmetic or dermatological field such as fat material, organic solvent, dissolvent, concentrate, gellant, softening agent, anti-oxidant, suspending agent, stabilizing agent, foaming agent, flavoring agent, surfactant, water, ionic or non-ionic emulsifier, filler, metal ion sequestering agent, chelating agent, preservative, vitamin, blocking agent, moisturizing agent, essential oil, dye stuff, pigment, hydrophilic or hydrophobic activator, lipid vesicle or optional other components which are commonly used in cosmetics. The above adjuvants are introduced in the amount generally used in the cosmetic or dermatological field.

In addition, the composition of the present invention can contain materials facilitating the skin absorption.

[Mode for Practicing the Invention]

Hereinafter, an explanation on the constitution and effects of the present invention will be described in detail with reference to experimental or formulation examples. However, such experimental or formulation examples are merely provided as an illustrative object in order to help the understanding of the present invention and are not intended to limit the scope and range of the present invention.

Reference Example 1 Isolation of Ergosterol-Based Compound and Identification of its Structure 1. Extraction 70% Ethanol solution was added to 4 kg of powder which is made of whole sites of *Lentinula edodes* (place of origin: Jeju island) to extract an extract at room temperature for 24 hours, and then the obtained extract was filtered. All the filtrates were combined, were vacuum evaporated at 40° C. to obtain 1075 g of *Lentinula edodes* extract.

The obtained extract was distributed and extracted with water (3 L) and ethyl acetate (3 L×6) to obtain ethyl acetate fraction (9 g) and water fraction.

2. Isolation and Purification

Ethyl acetate fractions obtained from above (BHE, 9 g) were subjected to a silica gel chromatography (Ψ7.5 cm×15 cm, n-hexane-EtOAc=10:1→7:1→5:1→3:1→CHCl$_3$—MeOH=40:1→30:1→20:1→10:1→7:1) to obtain thirty-six of fractions (BHE-1 to BHE-36).

(1) 3β, 5α-dihydroxy-6β-methoxy-(22E, 24M-ergosta-7,22-diene

1) Isolation

BHE-16 [762 mg, Ve/Vt 0.136-0.184] among the fractions obtained from the above was subjected to Octadecyl silica gel (ODS) column chromatography (Ψ3.5 cm×12 cm, acetone:MeOH=2:3) to obtain seven fractions (BHE-16-1 to BHE-16-7). The second fraction, BHE-16-2 [143.4 mg, Ve/Vt 0.167-0.208] among these was subjected to silica gel column chromatography (Ψ3.5 cm×12 cm, n-hexane:EtOAc=2:1) to obtain eleven fractions (BHE-16-2-1 to BHE-16-2-11), and ergosterol compound, 3β, 5α-dihydroxy-6β-methoxy-(22E, 24R)-ergosta-7,22-diene (BHE- 16-2-9, 30 mg, Ve/Vt 0.662-0.822) was isolated as a white powder from 9$^{th}$ fraction among these (molecular weight: 444).

2) Structure Identification

The structure of ergosterol compound isolated from above was identified by using NMR. NMR used 400 MHz FT-NMR spectroscope (Varian Inova AS-400, Palo Alto, Calif.), the compound was dissolved in $CDCl_3$, pyridine-$d_5$, heavy hydrogenation solvent (Merck, Darmstadt, Germany).

White powder; m.p. 173~176° C.; $[\alpha]_D^{20}$ −61.0° (c=1.19, $CHCl_3$); IR (film, $v_{max}$, $cm^{-1}$) 3400, 1640; EI-MS m/z 444 $[M]^+$; $^1$H-NMR (400 MHZ, $CDCl_3$) 5.37 (1H, br.d, J=5.2 Hz, H-7), 5.20 (1H, dd, J=15.2, 7.2 Hz, H-23), 5.13 (1H, dd, J=15.2, 8.0, H-22), 4.02 (1H, m, H-3), 3.36 (3H, s, H-6-$OCH_3$), 3.14 (1H, d, J=5.2 Hz, H-6), 0.99 (3H, d, J=6.8 Hz, H-21), 0.97 (3H, s, H-19), 0.89 (3H, d, J=6.8 Hz, H-28), 0.81 (3H, d, J=6.4 Hz, H-27), 0.79 (3H, d, J=6.4 Hz, H-26), 0.57 (3H, s, H-18); $^{13}$C-NMR (100 MHz, $CDCl_3$) 143.6 (C-8), 135.4 (C-22), 132.0 (C-23), 114.9 (C-7), 82.4 (C-6), 76.1 (C-5), 67.7 (C-3), 58.2 (6-$OCH_3$), 55.9 (C-17), 54.9 (C-14), 43.8 (C-9), 42.8 (C-13), 40.3 (C-24), 39.5 (C-20), 39.3 (C-12), 37.2 (C-4), 33.0 (C-10), 32.7 (C-25), 30.8 (C-1), 29.6 (C-2), 27.9 (C-16), 22.8 (C-15), 22.1 (C-11), 21.0 (C-21), 19.9 (C-27), 19.6 (C-26), 18.3 (C-19), 17.5 (C-28), 12.2 (C-18)

(2) 3β, 5α, 9α-trihydroxy-(22E, 24R)-ergosta-7,22-diene-6-one

1) Isolation

BHE-24 [224.2 mg, Ve/Vt 0.457-0.484] among the fractions obtained from the above was subjected to Sephadex LH-20 column chromatography (Ψ1.5 cm×65 cm, 80% MeOH) to obtain seven fractions (BHE-24-1 to BHE-24-7). Ergosterol compound, 3β, 5α, 9α-trihydroxy-(22E, 24R)-ergosta-7,22-diene-6-one was isolated from the second fraction, BHE-24-2 [50 mg, Ve/Vt 0.623-0.666] among them (molecular weight: 444).

2) Structure Identification

The structure of ergosterol compound isolated from the above was identified by using NMR. NMR used 400 MHz FT-NMR spectroscope (Varian Inova AS-400, Palo Alto, Calif.), the compound was dissolved in $CDCl_3$, pyridine-$d_5$, heavy hydrogenation solvent (Merck, Darmstadt, Germany).

Colorless crystal; m.p. 181~182° C., $[\alpha]_D^{20}$ −115° (c=0.42, $CHCl_3$); IR (KBr, $v_{max}$, $cm^{-1}$) 3400, 2871, 1720, 1663, 1461, 1377, 1053, 1024, 970, 756; EI-MS m/z 444 $[M]^+$; $^1$H-NMR (400 MHZ, pyridine-$d_5$) 8.51 (s, 5-OH), 6.23 (s, 9-OH), 5.93 (1H, d, J=1.2 Hz, H-7), 5.31 (1H, dd, J=15.2, 7.2 Hz, H-23), 5.24 (1H, dd, J=15.2, 8.0 Hz, H-22), 4.65 (1H, m, H-3), 3.02 (1H, t, J=9.2 Hz, H-14), 2.97 (1H, m, H-1α), 2.83 (1H, dd, J=14.0, 4.0 Hz, H-4α), 2.32 (1H, dd, J=14.0, 9.2 Hz, H-4β), 1.96 (2H, m, H-2), 2.06 (1H, m, H-20), 1.91 (1H, m, H-24), 1.16 (3H, s, H-18), 1.06 (3H, d, J=6.4 Hz, H-21), 0.97 (3H, d, J=6.8 Hz, H-28), 0.88 (3H, d, J=6.8 Hz, H-27), 0.87 (3H, d, J=6.8 Hz, H-26), 0.65 (3H, s, H-19); $^{13}$C-NMR (100 MHz, pyridine-$d_5$) 199.0 (C-6), 164.1 (C-8), 135.9 (C-23), 132.5 (C-22), 120.3 (C-7), 79.8 (C-5), 75.1 (C-9), 66.8 (C-3), 56.2 (C-17), 52.0 (C-14), 45.4 (C-13), 43.1 (C-24), 42.3 (C-10), 40.6 (C-20), 38.2 (C-4), 35.5 (C-12), 33.4 (C-25), 31.5 (C-2), 29.0 (C-11), 28.3 (C-16), 26.4 (C-1), 22.7 (C-15), 21.3 (C-21), 20.4 (C-18), 20.1 (C-27), 19.9 (C-26), 17.9 (C-28), 12.4 (C-19)

Reference Example 2 Cell Culture (Melan-a Cell)

Melanin-forming cell (melanocyte) derived from C57BL/6J mouse, melan-a cell was cultured by using RPMI-1640 medium (Lonza, USA) with 10% FBS (Fetal Bovine Serum; bovine fetal serum) and 50 U/ml penicillin, 50 μg/ml streptomycin under the condition of 37° C., 10% $CO_2$ and then used in the following experiment.

Experimental Example 1 Cytotoxic Test (MTT Assay) for Ergosterol-Based Compound

In order to determine the cell treatment concentration of 3β, 5α-Dihydroxy-6β-methoxy-(22E, 24R)-ergosta-7,22-diene and 3β, 5α, 9α-trihydroxy-(22E, 24R)-ergosta-7,22-diene-6-one, MTT assay was used.

Melan-a cell cultured by the method of the Reference Example 2 was seeded on 96 well plates so as to be 1.0×10$^4$ of cell number and then, cultured for 24 hours. And then, it was treated by new medium containing various concentrations of 3β, 5α-dihydroxy-6β-methoxy-(22E, 24R)-ergosta-7,22-diene or 3β, 5α, 9α-trihydroxy-(22E, 24M-ergosta-7, 22-diene-6-one isolated from the Reference Example 1, and was cultured for 72 hours. At this time, in order to compare it, it was treated by a medium containing a 0.1% solution in which DMSO and EtOH were mixed at the ratio of 1:3 and cultured. Each well of 96 well plates which was cell-culturing was exchanged with a medium containing methylthiazolyldiphenyltetrazolium bromide (MTT) and then reacted for 2 hours. After the reaction, all the mediums in 96 well plates were removed, and DMSO was added to each well to dissolve the stained cells. Absorbance (OD 570) was determined by using microplate reader (Product Name: Synergy 2 (BioTek)), and a survival rate of the cell was determined by comparing it with the control. The determination results are represented in FIG. 1.

The concentration of sample in which the survival rate of the cell is 80% or more was ascertained from the results represented in FIG. 1, and the sample was used to the concentration of up to 10 μM in the following experiment.

Experimental Example 2 Cytotoxicity Test (MTT Assay) for Arbutin and *Lentinula edodes* Extract MTT assay was performed for *Lentinula edodes* extract and arbutin obtained by adding 70% ethanol solution to *Lentinula edodes* in the Reference Example 1

The method similar to the Experimental Example 1 was used, except that 50 ppm arbutin, *Lentinula edodes* extracts (12.5, 25, 50, 100 ppm) were used as the sample treated. Absorbance (OD 570) was measured by using microplate reader (Product Name: Synergy 2 (BioTek)), and a survival rate of the cell was determined by comparing it with the control. The determination results are represented in FIG. 2.

It can be identified from the results represented in FIG. 2 that 50 ppm arbutin and all ranges of the concentrations of *Lentinula edodes* extract tested did not affect the cell growth.

Experimental Example 3 Melanin Analysis of Melan-A Cell

The Melan-a cell cultured by the method of the Reference Example 2 was seeded on 48 well plate so as to be 1.5×10$^4$ of the cell number per well and then, cultured for 24 hours. Then, a new medium containing various concentrations (0.1, 1, 10 μM) of 3β, 5α-dihydroxy-6β-methoxy-(22E, 24R)-ergosta-7,22-diene or 3β, 5α, 9α-trihydroxy-(22E, 24R)-ergosta-7,22-diene-6-one isolated from the Reference Example 1 was treated. At this time, in order to compare it, a medium containing 50 ppm of arbutin or 50 ppm of kojic acid was used as a positive control. The medium was treated for 6 days, and after three days, a new medium was exchanged. After 6 days, the cell was washed with DPBS and then, was added with 2N NaOH (10% DMSO) and dissolved at 60° C. for 1 hour. The cell lysate dissolved was moved into 96 well plates and then its absorbance (OD 475) was measured. The measured value was calculated as melanin content from the standard curve for the synthesized melanin, and the melanin content calculated was standardized by the total amount of the protein of each experimental group, and then it was compared with the control to estimate the efficiency. The results are represented in FIG. 3.

In addition, in order to compare the whitening effect of 3β, 5α-dihydroxy-6β-methoxy-(22E, 24R)-ergosta-7,22-diene and 3β, 5α, 9α-trihydroxy-(22E, 24R)-ergosta-7,22-diene-6-one with that of *Lentinula edodes* extract, the separate melan-a cell melanin assay experiment was performed with the same method as the above. At this time, 50 ppm of arbutin or 12.5, 25, 50, 100 ppm of ethanol extracts of *Lentinula edodes* obtained from the Reference Example 1 were used, and used by containing them in the medium for the cell culture. The results were represented in FIG. 4.

Upon reviewing FIG. 3, 3β,5α-dihydroxy-6β-methoxy-(22E, 24R)-ergosta-7,22-diene or 3β,5α,9α-trihydroxy-(22E, 24R)-ergosta-7,22-diene-6-one used in the present invention exhibits the effect of inhibiting a melanin production, and it can be identified as being concentration-dependent.

Meanwhile, upon reviewing FIG. 4, *Lentinula edodes* extract exhibits the efficiency inhibiting a melanin production, inhibits the melanin production in concentration-dependent manner, and in particular, when treating with 100 ppm, it can be identified that the melanin production was reduced to the extent of 74.5% when comparing it with that of the control (p-value<0.5).

However, when comparing FIG. 3 with FIG. 4, 10 μM of 3β,5α-dihydroxy-6β-methoxy-(22E, 24R)-ergosta-7,22-diene or 10 μM 3β,5α,9α-trihydroxy-(22E, 24R)-ergosta-7,22-diene-6-one corresponds to 4.44 ppm, and it can be seen that in the case of *Lentinula edodes* extract, there is little of the effect inhibiting the melanin production in the concentration of 25 ppm or less, but in the case of 3β,5α-dihydroxy-6β-methoxy-(22E, 24R)-ergosta-7,22-diene or 3β,5α, 9α-trihydroxy-(22E, 24R)-ergosta-7,22-diene-6-one, there is a remarkable effect inhibiting the melanin production by only the amount of 4.44 ppm. Moreover, it can be identified that 3β, 5α-dihydroxy-6β-methoxy-(22E, 24R)-ergosta-7, 22-diene or 3β, 5α, 9α-trihydroxy-(22E, 24M-ergosta-7,22-diene-6-one can provide the remarkably excellent skin whitening effect than albumin and kojic acid, by using much less amount than the amounts of albumin and kojic acid.

The invention claimed is:

1. A method for whitening a skin, which comprises a step for applying to the skin a cosmetic composition containing, as a sole skin whitening effective ingredient, 3β, 5α-dihydroxy-6β-methoxy-(22E, 24R)-ergosta-7, 22-diene or 3β,5α,9α-trihydroxy-(22E, 24R)-ergosta-7, 22-diene-6-one, and a cosmetically acceptable medium or base; wherein the concentration of the skin whitening effective ingredient is greater than 1 μm based on the total weight of the cosmetic composition.

2. The method of claim 1, wherein the effective ingredient is isolated from *Lentinula edodes* (Berk.) Sing.

3. The method of claim 1, wherein the concentration of the effective ingredient is greater than 10 μm based on the total weight of the cosmetic composition.

* * * * *